United States Patent [19]
Brocher

[11] Patent Number: 5,934,281
[45] Date of Patent: Aug. 10, 1999

[54] BELTED ARTHROSCOPIC MOBILIZER

[76] Inventor: Michelle Brocher, 51 Northtown Dr. #7C, Jackson, Miss. 39211

[21] Appl. No.: 09/034,879

[22] Filed: Mar. 4, 1998

[51] Int. Cl.$^6$ .................................................. A61B 19/00
[52] U.S. Cl. ........................... 128/869; 128/882; 602/23; 602/27
[58] Field of Search .................................. 128/845, 846, 128/869, 878, 879, 882; 602/32–40; 5/624

[56] References Cited

U.S. PATENT DOCUMENTS

| | | | |
|---|---|---|---|
| 3,355,163 | 11/1967 | Leinassar | 5/624 |
| 4,457,302 | 7/1984 | Caspari | 128/882 |
| 4,573,482 | 3/1986 | Williams, Jr. | |
| 4,709,693 | 12/1987 | Key | |
| 4,766,891 | 8/1988 | Schultz | 128/882 |
| 4,844,056 | 7/1989 | Peters | 602/32 |
| 5,582,579 | 12/1996 | Chism | 602/36 |

Primary Examiner—Michael A. Brown
Attorney, Agent, or Firm—David W. Carstens; Carstens, Yee & Cahoon

[57] ABSTRACT

A belted arthroscopic mobilizer is used to suspend a patient's leg from the waist of the surgeon or other user. The mobilizer allows the user to straighten, flex and otherwise manipulate the position of the patient's knee during arthroscopic surgery. The mobilizer has a shoe which craddles or cups the patient's foot. The shoe and an attached bracket are slidably coupled to a belt worn by the surgeon or other user.

14 Claims, 5 Drawing Sheets

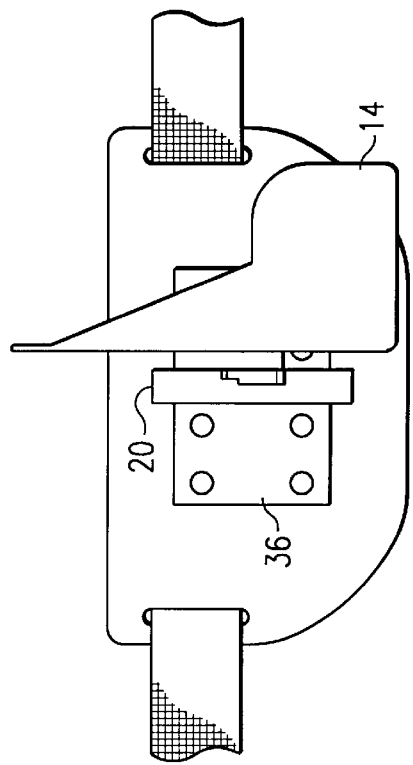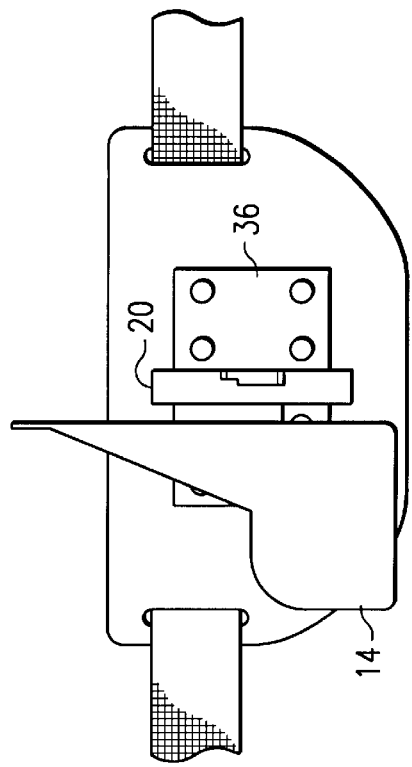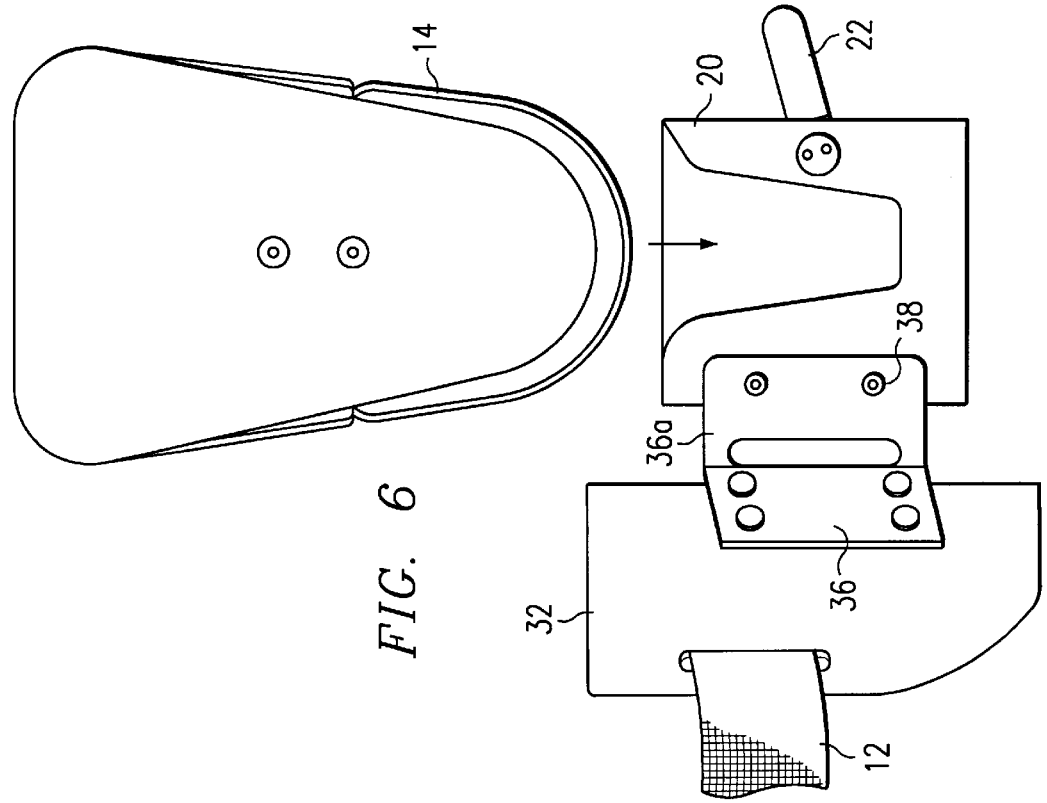

BELTED ARTHROSCOPIC MOBILIZER

BACKGROUND OF THE INVENTION

1. Technical Field

The present invention relates generally to a device used in arthroscopic knee surgery and specifically to a belted arthroscopic mobilizer that allows the surgeon to position and flex a patient's knee during a surgical procedure.

2. Description of the Related Art

Arthroscopic surgery has gained in popularity and effectiveness in the past decade. This style of surgery involves the insertion of a small surgical tool and a fiber optic camera into the injury region. The fiber optic camera allows the surgeon to view the injury and to monitor the progress and effect of the surgical tool. The surgeon guides the surgical tool to the injury site and performs the appropriate repairs. The ability to monitor the procedure through the fiber optic camera eliminates the need to radically open the site. Thus, only minor surface incisions are used to enter and egress the tool and camera.

During arthroscopic knee surgery, the surgeon often flexes the knee to measure the extent of the injury and also to obtain access to certain structures within the knee. However, an assistant must be used to flex the knee because the surgeon's hands are in use manipulating the camera and surgical tool. The likelihood of poor surgical results is increased if the surgeon and assistant improperly communicate regarding the desired positioning. Further, the cost of the surgery is incrementally increased when an additional assistant is required.

Attempts have been made to improve arthroscopic knee surgery through the use of a belt and straps to bind the patients foot to the surgeon. For example, U.S. Pat. No. 4,573,482 to Williams, Jr. discloses a method of arthroscopic knee surgery wherein the doctor wears a belt with at least one strap fixed to the belt. The patient's foot is immobilized within the strap, and thus suspended near the surgeon's waist. The Williams design though is flawed in that it fixes the position of the surgeon relative to the knee. He cannot, for example, walk around the knee to probe it from a different angle. Likewise, U.S. Pat. No, 4,709,693 to Key discloses a similar belt with straps fixed and immovable relative to the belt.

A need exists for an improved means for supporting a patient's leg during an arthroscopic procedure. The improved device should allow the surgeon to easily support weight of the leg, while also allowing him to adjust his perspective of the leg. The device should comfortably hold the patient's foot and yet provide a means to replace padding that could become soiled.

SUMMARY OF THE INVENTION

The present invention relates to a belted arthroscopic mobilizer. The mobilizer is typically worn around the waist of the user on a belt. The mobilizer uses a shoe to cup and support a patient's foot. The shoe is coupled to the belt by a first bracket which is slidable on the belt. The slidable nature of the shoe allows the user to reposition himself relative to the patient's leg, and further to flex and extend the leg without the use of his hands. By freeing the user's hands, the mobilizer allows him to concentrate on the more important aspects of performing arthroscopic surgery.

In an alternate embodiment, a second bracket is used to extend the shoe away from the user's body. Further, a shield can be incorporated in the design to minimize the chance of the shoe rolling even slightly. The belt can be threaded through the shield and the second bracket can be bolted the shield. The shoe can be removably attached to the first bracket. A locking mechanism can be used to lock the shoe in place. Likewise, a cushion can be set within or affixed to the cup surface of the shoe.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

FIG. 6 is an exploded view of the shoe and bracket assembly; and

FIGS. 7 and 8 illustrate the shoe both right-mounted and left-mounted on the support bracket.

DETAILED DESCRIPTION

Figure 1:
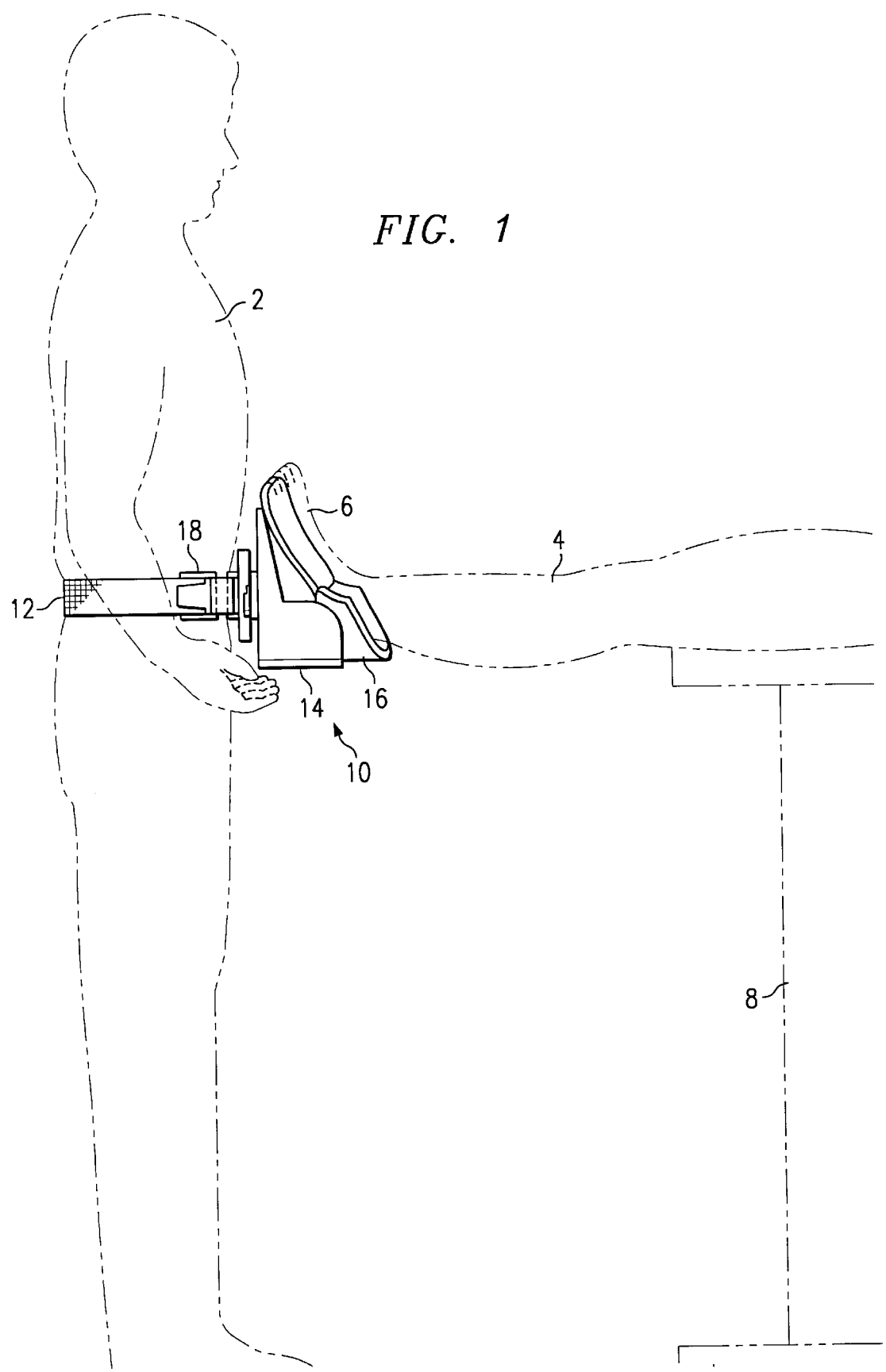
FIG. 1 is a side view of a user having a first embodiment of the mobilizer strapped to his waist.
Figure 2:
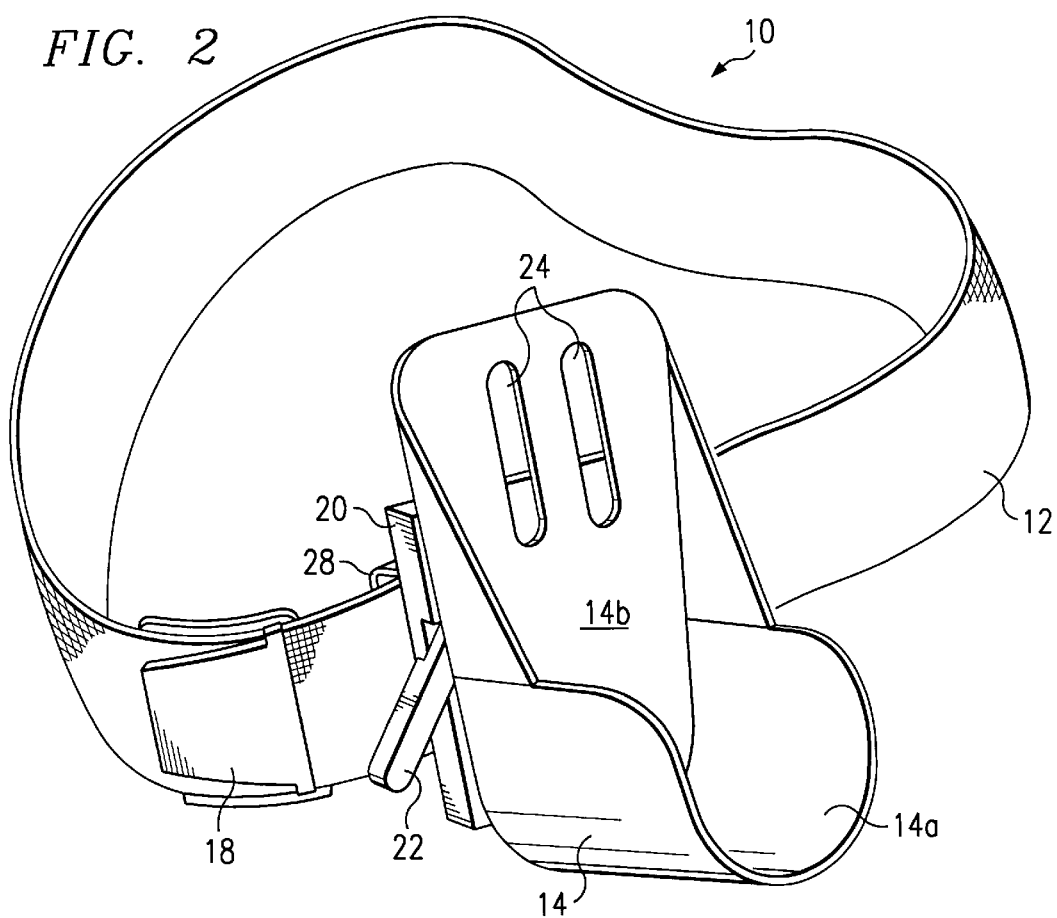
FIG. 2 is a perspective view of the mobilizer showing the shoe used to cup the patient's foot and the slidable bracket attaching the shoe to the belt.
Figure 3:
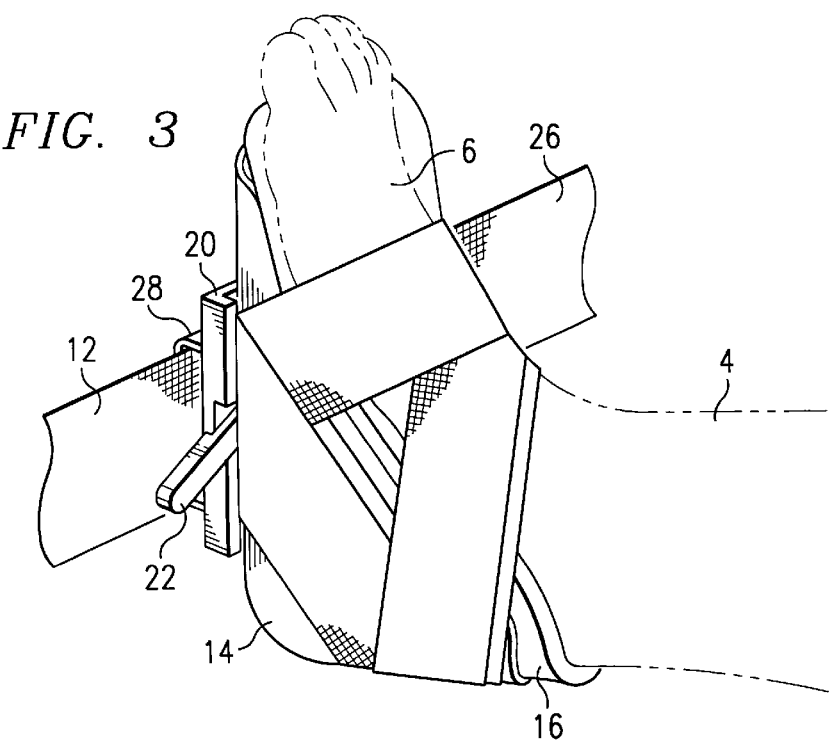
FIG. 3 is a perspective view showing the patient's foot immobilized in the shoe.

A belted arthroscopic mobilizer 10 embodying the present invention is shown in FIGS. 1, 2 and 3. The mobilizer 10 includes a shoe 14 that is slidably mounted to a belt 12. The belt is shown around the waist of a user 2 and is tightened in place by clasp 18. A patient's leg 4 is suspended from a table 8 at approximately the height of the user's waist. The patient's foot 6 is cupped in the shoe 14. A removable cushion 6 can be placed in the shoe.

FIG. 2 provides a more detailed view of the shoe 14 without a cushion 18. The shoe has a hemicylindrical portion 14a upon which the patient's heel rests. The shoe further has a flat portion 14b against which the bottom of the foot rests. The flat portion 14b can include holes 24. The shoe 14 fits into a first bracket 20 that includes a locking mechanism 22 used to lock the shoe to the bracket 20. Any suitable locking mechanism can be used. A loop 28 extends from the back of the bracket 20. The loop 28 is sized to allow the passage of the belt 12. Finally, the patient's foot 6 can be immobilized in the shoe 14 by straps 26. The straps can be integrated into the design of the shoe 14, cushion 16, or bracket 20. Alternatively, the straps can simply be wrapped around the shoe 14. Space can be provided between the bracket 20 and the shoe 14 in order to ease the wrapping process.

Figure 4:
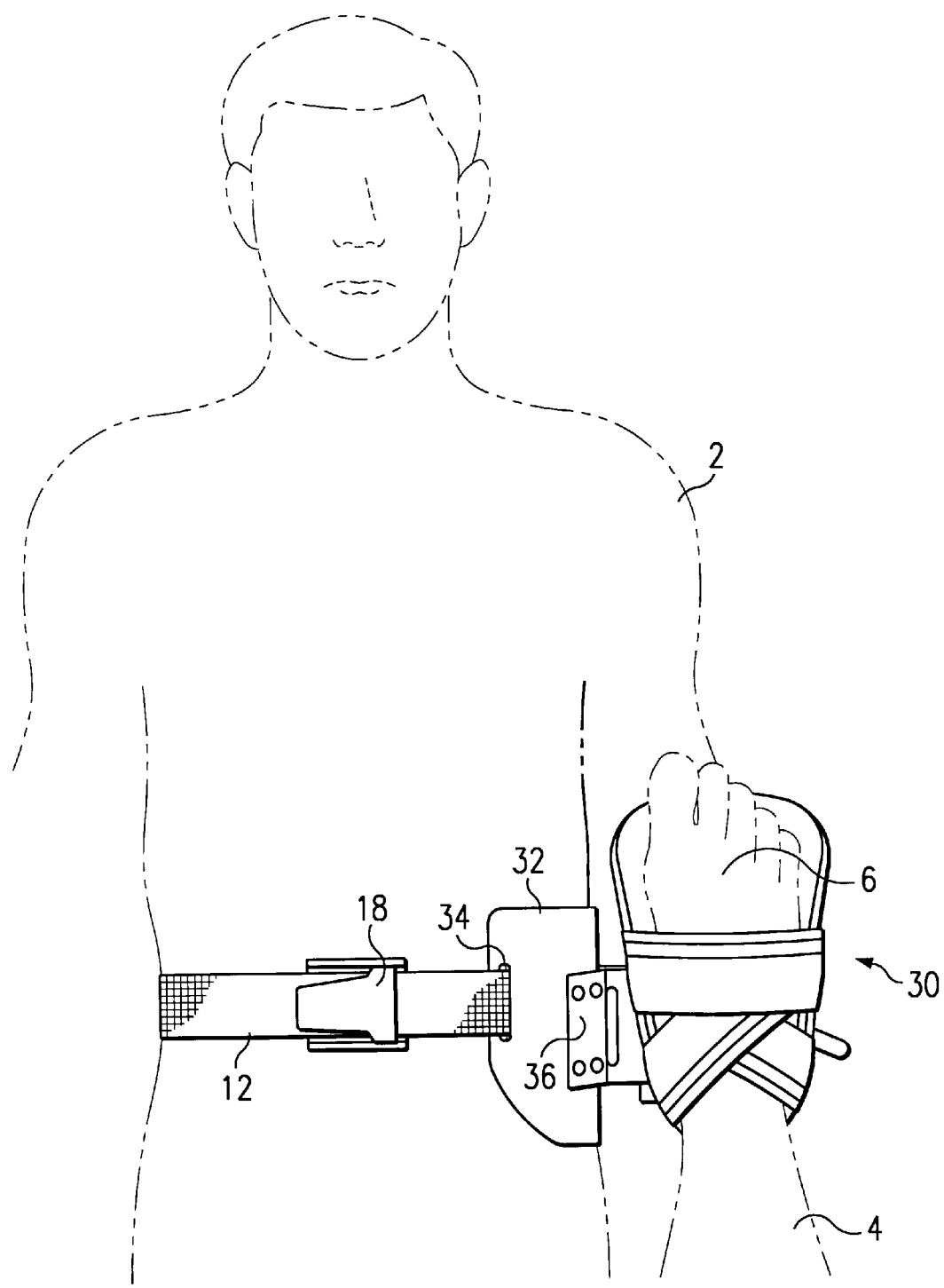
FIG. 4 shows an alternate embodiment of the present invention wherein the shoe is attached to a shield portion by means of a bracket or hinge.
Figure 5:
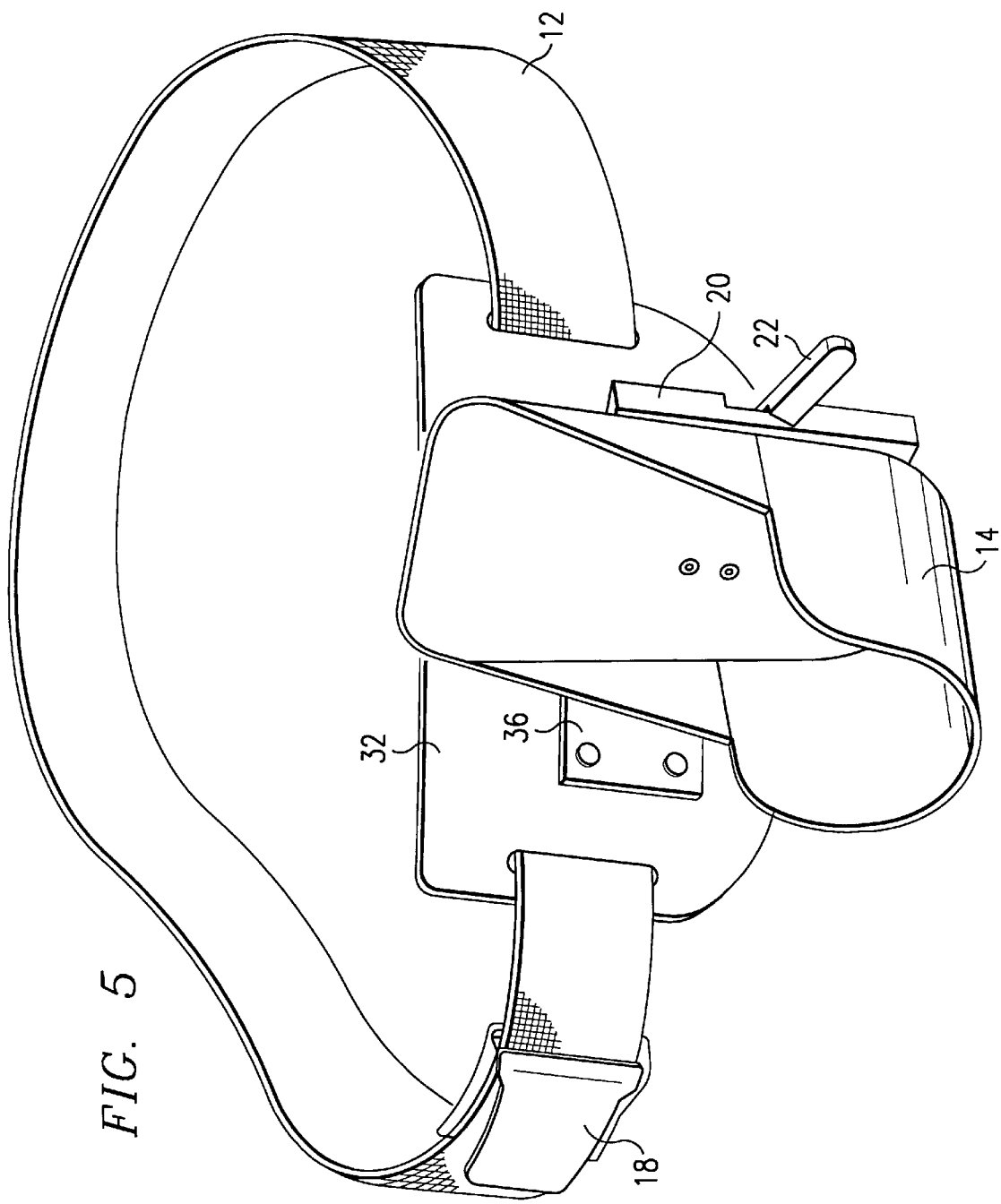
FIG. 5 is a perspective of the embodiment shown in FIG. 4.

FIGS. 4 to 8 illustrate an alternate embodiment of the invention wherein the shoe is suspended away from the belt by means of a second bracket or hinge. This design allows the leg to be more easily suspended to the side of the user 2. Referring to FIGS. 4 and 5, a belt 12 is used to harness the mobilizer 30 to the user 30. While the belt is shown around the user's waist, it could also be draped over the user's shoulder or any other load-bearing portion of the user. A clasp 18 is used to tighten the belt in place. A shield can be used to couple the shoe 14 to the belt 12. The shield can also distribute the torque applied to the user from the suspended leg 4. The shield also helps minimize the tendency of the shoe 14 to roll. The belt 12 loops through holes 34 in the shield 32. A second bracket 36 is coupled to the shield. The shoe 14 is mounted to a first bracket 20 and locked down with locking mechanism 22.

FIG. 6 provides an exploded view of the shoe 14, first bracket 20 and second bracket 36. The second bracket 36 is fixed to the shield 32 and has a portion 36a that extends outward from the shield 32. Second bracket 3 can also be hinged, allowing portion 36a to pivot relative to the shield 32. The first bracket 20 is fixed to second bracket portion 36a. The shoe can be extended from the user's body by any suitable distance, but a distance between 1 and 6 inches is preferred. FIGS. 7 and 8 illustrate the right-mounted and left-mounted versions of the invention, respectively. The ability to adjust the orientation of the shoe 14 allows the foot to be held to the left or right side of the user during a procedure.

The mobilizers 10, 30 can be fabricated out of many different materials. For example, the shoe could be stamped aluminum or molded plastic. The cushion could be any synthetic foam. The cushion could be held to the shoe with a light adhesive, hook and loop fasteners or not at all. The belt 12 could be leather or a synthetic fabric. In view of the fact that invention is used during operations, all parts should be either disposable or sterilizable.

In use, the patient lays on the table 8 so that his leg extends over its edge. His foot is immobilized in the shoe 14. The user 2, typically the surgeon, can extend the leg 4 straight or flex the leg at the knee while performing the operation simply by moving forward or back. The user 2 can change perspective by moving around the leg 4 because the mobilizer 10, 30 can slide relative to the belt. And while the previous discussion has focused on the use of the invention in knee surgery, it is also suited for operations on elbows and other parts of a body. Further, the patient can be human, or any other animal.

The description of the present invention has been presented for purposes of illustration and description, but is not limited to be exhaustive or limited to the invention in the form disclosed. Many modifications and variations will be apparent to those of ordinary skill in the art. The embodiment was chosen and described in order to best explain the principles of the invention the practical application to enable others of ordinary skill in the art to understand the invention for various embodiments with various modifications as are suited to the particular use contemplated.

I claim:

1. A belted arthroscopic mobilizer comprising:
   (a) belt;
   (b) a shoe slidably coupled to the belt by a first bracket.
2. The mobilizer of claim 1 wherein said belt further comprises a clasp.
3. The mobilizer of claim 1 wherein said shoe comprises a hemicylindrical portion.
4. The mobilizer of claim 1 wherein said first bracket is coupled to the belt with a second bracket.
5. The mobilizer of claim 4 further comprises a shield portion attached to the second bracket.
6. The mobilizer of claim 4 wherein said second bracket is a hinge.
7. The mobilizer of claim 1 further comprises a cushion in said shoe.
8. The mobilizer of claim 1 wherein said shoe is right mounted.
9. The mobilizer of claim 1 wherein said shoe is left-mounted.
10. The mobilizer of claim 1 wherein said shoe is a plastic.
11. The mobilizer of claim 1 wherein said shoe is suspended a distance from said belt.
12. A method of performing an arthroscopic surgery comprising the steps of:
    (a) suspending a patient's leg in a shoe slidably coupled to a belt on a user by a first bracket;
    (b) sliding the position of the shoe in response to a movement by the user.
13. The method of claim 12 further comprises:
    (c) performing arthroscopic surgery on said patient.
14. The method of claim 13 further comprises:
    (d) flexing said leg during the surgery.

* * * * *